(12) United States Patent
Yanagawa et al.

(10) Patent No.: US 6,977,160 B2
(45) Date of Patent: Dec. 20, 2005

(54) SENSOR PROTEIN AND USE THEREOF

(75) Inventors: Hiroshi Yanagawa, Kanagawa (JP); Nobuhide Doi, Yokohama (JP); Naoto Nemoto, Machida (JP)

(73) Assignee: Mitsubishi Chemical Corporation, Tokyo (JP)

( * ) Notice: Subject to any disclaimer, the term of this patent is extended or adjusted under 35 U.S.C. 154(b) by 438 days.

(21) Appl. No.: 09/853,939

(22) Filed: May 11, 2001

(65) Prior Publication Data

US 2005/0142623 A1 Jun. 30, 2005

Related U.S. Application Data

(63) Continuation-in-part of application No. PCT/JP99/06261, filed on Nov. 10, 1999.

(30) Foreign Application Priority Data

Nov. 11, 1998 (JP) ................................. 10/320102

(51) Int. Cl.$^7$ ................... C12P 21/06; C07H 21/04; C07K 19/00; G01N 33/53
(52) U.S. Cl. ............... 435/69.7; 435/320.1; 435/252.3; 435/7.9; 536/23.4; 530/350; 530/399; 530/400; 424/192.1
(58) Field of Search .................. 530/350, 399, 530/400; 435/69.7, 252.3, 320.1, 7.9; 536/23.1, 536/23.4; 424/192.1

(56) References Cited

U.S. PATENT DOCUMENTS

| 5,362,644 A | 11/1994 | Boquet et al. ............ 435/252.3 |
| 5,534,223 A | 7/1996 | Boquet et al. ................ 422/61 |

FOREIGN PATENT DOCUMENTS

| EP | 407259 A1 | 1/1991 |
| WO | 94/20636 | 9/1994 |
| WO | 99/24617 | 5/1999 |
| WO | 00/71565 | 11/2000 |

OTHER PUBLICATIONS

Burbach et al: "Cloning of the AH-receptor cDNA reveals a distinctive ligand-activated transcription factor" Proceedings of the National Academy of Sciences of USA, National Academy of Science. Washington, US, vol. 17, No. 89, Sep. 1992, pp. 8185-8189, XP001069093. ISSN: 0027-8424.

Hellinga et al: "Protein engineering and the development of generic biosensors" Trends in Biotechnology, Elsevier Publications, Cambridge, GB, vol. 16, No. 4, Apr. 1998, pp. 183-189, XP004112305. ISSN: 0167-7799.

Baird et al: "Circular permutation and receptor insertion within green fluorescent proteins" Proceedings of the National Academy of Sciences of USA, National Academy of Science. Washington, US, vol. 96, No. 20, Sep. 1999, pp. 11241-11246, XP002187230. ISSN: 0027-8424.

(Continued)

*Primary Examiner*—Jon Weber
*Assistant Examiner*—Rita Mitra
(74) *Attorney, Agent, or Firm*—Wenderoth, Lind & Ponack, L.L.P.

(57) ABSTRACT

The object of the present invention is to utilize, as a sensor protein, a molecular recognizing ability of a protein that scarcely undergoes any structural change by the binding of a target substance. According to the present invention, there is provided a sensor protein comprising an insert-type fusion protein composed of a reporter protein and a biding protein wherein said binding protein is inserted into the amino acid sequence of said reporter protein.

10 Claims, 6 Drawing Sheets

OTHER PUBLICATIONS

Brennan et al., "A molecular sensor system based on genetically engineered alkaline phosphate", Proc. Natl. Acad. Sci. USA, vol. 92, pp. 5783-5787 (1995).

Doi et al., "Insertion of foreign random sequences of 120 amino acid residues into an active enzyme", FEBS Letters, vol. 402, pp. 177-180 (1997).

Abedi et al., "Green fluorescent protein as a scaffold for intracellular presentation of peptides", Nucleic Acids Research, vol. 26, No. 2 pp. 623-630 (1998).

Adams et al., "Fluorescence ratio imaging of cyclic AMP in single cells", Nature, vol. 349, pp. 694-697 (1991).

Marvin et al., "The rational design of allosteric interactions in a monomeric protein and its applications to the construction of biosensors", Proc. Natl. Sci. USA, vol. 94, pp. 4366-4371 (1997).

Miyawaki et al. "Fluorescent indicators for $Ca^{2+}$ based of green fluorescent proteins and calmodulin", Nature, vol. 388, pp. 882-887 (1997).

Romoser et al., "Detection of Living Cells of $Ca^{2+}$-dependent Changes in the Fluorescence Emission of an Indicator Composed of Two Green Fluorescent Protein Variants Linked by a Calmodulin-binding Sequence", The Journal of Biological Chemistry, vol. 272, No. 20, pp. 13270-13274 (1997).

Botstein et al., "Strategies and Applications of in Vitro Mutagenesis", Science, vol. 229, No. 4719, pp. 1193-1201 (1985).

Leung et al., "A Method For Random Mutagenesis Of A Defined DNA Segment Using A Modified Polymerase Chain Reaction", Technique, vol. 1, No. 1 pp. 11-15 (1989).

Zhou et al., "In Vitro evolution of thermodynamically stable turns", Nature Structural Biology, vol. 3, No. 5, pp 446-451 (1996).

Axe et al., "Active barnase variants with completely random hydrophobic cores", Proc. Natl. Acad. Sci. USA, vol. 93, pp. 5590-5594 (1996).

Stemmer, "Rapid evolution of a protein in vitro by DNA shuffling", Nature, vol. 370, pp. 389-391 (1994).

Birge, "Protein-Based Computer", Scientific American, pp. 66-71 (1995).

Itaya et al., "A neomycin resistance gene cassette selectable in a single copy state in the *Bacillus subtilis* chromosome", Nucleic Acids Research, vol. 17, pp. 4410 (1989).

Prijambada et al., "Solubility of artificial protiens with random sequences" FEBS Letters, vol. 382, pp. 21-25, (1996).

Strynadka et al., "A potent new mode of β-lactamase inhibition revealed by the 1.7 Å X-ray crystallographic structure of the TEM-1-BLIP complex", Nature Structural Biology, vol. 3, No. 3, pp. 290-297 (1996).

Barany, "Single-Stranded hexameric linkers: a system for in-phase insertion mutagenesis and protein engineering", Gene, vol. 37. pp. 111-123 (1985).

Crameri et al., "Improved Green Fluorescent Protein by Molecular Evolution Using DNA Shuffling", Nature Biotechnology, vol. 14, pp. 315-319 (1996).

Doran et al., "Isolation and Characterization of a β-Lactamase-Inhibitory Protein from *Streptomyces clavuligerus* and Cloning and Analysis of Corresponding Gene", Journal of Bacteriology, vol. 172, No. 9 pp. 4909-4918 (1990).

Guzman et al,. "Tight Regulation, Modulation, and High-Level Expression by Vectors Containing the Arabinose $P_{BAD}$ Promoter", Journal of Bacteriology, vol. 177, No. 14, pp. 4121-4130 (1995).

Buchholz et al., "Improved properties of FLP recombinase evolved by cycling mutagenesis", Nature Biotechnology, vol. 16, pp. 657-662 (1998).

Chang et al., "Nucleotide sequence of the alkaline phosphatase gene of *Escherichia coli*", Gene, vol. 44, pp. 121-125 (1986).

Dolwick et al., "In vitro analysis of Ah receptor domains involved in ligand-activated DNA recognition", Proc. Natl. Acad. Sci. USA, vol. 90, pp. 8566-8570 (1993).

Benito et al., "β-Galactosidase Enzymatic Activity as a Molecular Probe to Detect Specific Antibodies", The Journal of Biological Chemistry, vol. 271, No. 35, pp. 21251-21256 (1996).

Siegel et al., "A Genetically Encoded Optical Probe of Membrane Voltage", Neuron, vol. 19, pp. 735-741 (1997).

Feliu et al., "Engineering of solvent-exposed loops in *Escherichia coli* β-galactosidase", FEBS Letters, vol. 434, pp. 23-27 (1998).

Betton et al., "Creating a bifunctional protein by insertion of β-lactamase into the maltodextrin-binding protein", Nature Biotechnology , vol. 15, pp. 1276-1279 (1997).

SEQUENCE LISTING

<160> NUMBER OF SEQ ID NOS: 13

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 1
gcgccatggt tgcataatgt gcctgtcaaa tggac                              35

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 2
cgccatatgt tcactccatc caaaaaaacg ggtatg                             36

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 3
gcccatatgg cggggtgat gaccg                                          25

-continued

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 4
gccgagctct tatacaaggt cccactgccg                                      30

<210> SEQ ID NO 5
<211> LENGTH: 54
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 5
gccgctagcc atcatcatca tcatcatggt atgagtaaag gagaagaact tttc           54

<210> SEQ ID NO 6
<211> LENGTH: 39
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 6
gccggtaccc caagcttttc aatgttgtgg cgaattttg                            39

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 7
gccggtacca gaattcgatg gaagcgttca actag                                35

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 8
gccgagctct ctagattatt tgtatagttc atccatgcc                            39

<210> SEQ ID NO 9
<211> LENGTH: 44
<212> TYPE: DNA
<213> ORGANISM: Artificial Sequence
<220> FEATURE:
<223> OTHER INFORMATION: Description of Artificial Sequence:synthetic
      DNA
<221> NAME/KEY: base
<222> LOCATION: (12)
<223> OTHER INFORMATION: n = a, g, c or t
<221> NAME/KEY: base
<222> LOCATION: (13)
<223> OTHER INFORMATION: n = a, g, c or t

```
<221> NAME/KEY: base
<222> LOCATION: (14)
<223> OTHER INFORMATION: n = a, g, c or t
<221> NAME/KEY: base
<222> LOCATION: (15)
<223> OTHER INFORMATION: n = a, g, c or t
<221> NAME/KEY: base
<222> LOCATION: (16)
<223> OTHER INFORMATION: n = a, g, c or t
<221> NAME/KEY: base
<222> LOCATION: (17)
<223> OTHER INFORMATION: n = a, g, c or t

<400> SEQUENCE: 9
gcatcccggg cnnnnnnttt aatcatcggc tcgtataatg tgtg        44

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence:synthetic
      DNA
<221> NAME/KEY: base
<222> LOCATION: (10)
<223> OTHER INFORMATION: n = a, g, c or t
<221> NAME/KEY: base
<222> LOCATION: (11)
<223> OTHER INFORMATION: n = a, g, c or t
<221> NAME/KEY: base
<222> LOCATION: (12)
<223> OTHER INFORMATION: b =  g, c or t
<221> NAME/KEY: base
<222> LOCATION: (13)
<223> OTHER INFORMATION: n = a, g, c or t
<221> NAME/KEY: base
<222> LOCATION: (14)
<223> OTHER INFORMATION: n = a, g, c or t
<221> NAME/KEY: base
<222> LOCATION: (15)
<223> OTHER INFORMATION: b = g, c or t
<221> NAME/KEY: base
<222> LOCATION: (16)
<223> OTHER INFORMATION: n = a, g, c or t
<221> NAME/KEY: base
<222> LOCATION: (17)
<223> OTHER INFORMATION: n = a, g, c or t
<221> NAME/KEY: base
<222> LOCATION: (18)
<223> OTHER INFORMATION: b = g, c or t

<400> SEQUENCE: 10
gccaagcttn nbnnbnnbca cccagaaacg ctggtg        36

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence:synthetic
      DNA
<221> NAME/KEY: base
<222> LOCATION: (10)
<223> OTHER INFORMATION: v = a, g or c
<221> NAME/KEY: base
<222> LOCATION: (11)
<223> OTHER INFORMATION: n = a, g, c or t
<221> NAME/KEY: base
<222> LOCATION: (12)
<223> OTHER INFORMATION: n = a, g, c or t
<221> NAME/KEY: base
<222> LOCATION: (13)
<223> OTHER INFORMATION: v = a, g or c
<221> NAME/KEY: base
<222> LOCATION: (14)
```

-continued

```
<223> OTHER INFORMATION: n = a, g, c or t
<221> NAME/KEY: base
<222> LOCATION: (15)
<223> OTHER INFORMATION: n = a, g, c or t
<221> NAME/KEY: base
<222> LOCATION: (16)
<223> OTHER INFORMATION: v = a, g or c
<221> NAME/KEY: base
<222> LOCATION: (17)
<223> OTHER INFORMATION: n = a, g, c or t
<221> NAME/KEY: base
<222> LOCATION: (18)
<223> OTHER INFORMATION: n = a, g, c or t

<400> SEQUENCE: 11
gccgaattcv nnvnnvnncc aatgcttaat cagtgaggc                                 39

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 12
aaactcgagt acaactataa ctc                                                  23

<210> SEQ ID NO 13
<211> LENGTH: 43
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 13
gcccatatgc atcatcatca tcatcatgcg ggggtgatga ccg                            43
```

SENSOR PROTEIN AND USE THEREOF

This application is a Continuation-In-Part of International Application Serial No. PCT/JP99/06261 filed Nov. 10, 1999.

TECHNICAL FIELD

The present invention relates to a sensor protein for detecting or quantifying a wide variety of target substances; a method of preparing said sensor protein; a nucleic acid encoding said sensor protein; an expression vector containing said nucleic acid; a transformed cell having said expression vector; a method of detecting or quantifying a target substance by using said sensor protein; and a reagent kit for performing said method of detection or quantification.

BACKGROUND ART

Biosensors such as sensor proteins are molecular sensors obtained by connecting molecular recognition mechanism and signal transduction technology. In order to construct a sensor protein by using highly specific molecular recognition ability of protein, it is necessary to link two sites, i.e., a binding site for recognizing a target substance and a reporter site for generating a signal.

There have been reported some examples of sensor proteins designed by means of protein engineering (Hellinga & Marvin 1998. Trends Biotechnol. 16, 183–189). For example, there have been known a cAMP sensor which uses the character that cAMP binds to a cAMP-dependent protein kinase to dissociate two subunits of the cAMP-dependent protein kinase (Adams et al. 1991. Nature 349, 694–697); a maltose sensor using the character that when maltose binds to a maltose-binding protein, the structure of the maltose-binding protein changes (Marvin et al. 1997. Proc. Natl. Acad. Sci. USA 94, 4366–4371); a calcium ion sensor using the structural change of calmodulin (Miyawaki et al. 1997. Nature 388, 882–887; Romoser et al. 1997. J. Biol. Chem. 272, 13270–13274) and the like.

DISCLOSURE OF THE INVENTION

In the conventional sensor proteins, there have been used only the proteins where the subunits dissociate or associate or the structures undergo a significant change when a target substance binds thereto. However, there are a number of proteins that hardly change their structures by the binding of a target substance. For utilizing the molecular recognition ability of such proteins as a sensor protein, it has been necessary to link the binding site for a target substance with a reporter site to allow the protein to attain a function as a sensor protein.

The present inventors found and already reported that it is possible to easily construct an insert-type fusion protein by expression of a recombinant DNA obtained by inserting a DNA sequence encoding one protein into a DNA sequence encoding another protein (Doi et al. 1997. FEBS Lett. 402, 177–180). In conventional fusion proteins in which two proteins are coupled to each other at their ends, it is known that the activity of each of these two proteins is hardly affected by the fusion. In contrast, it is expected that, in the insert-type fusion protein constructed by the present inventors, the activity of one protein into which another protein is inserted is largely affected depending upon the difference in structural stability of the protein to be inserted. The present inventors have diligently studied to construct a superior sensor protein by using such a character, and as a result, it has been found that sensor proteins can be designed as required by utilizing the character that when a protein having a binding site (binding protein) is inserted into the amino acid sequence of a protein having a reporter site (reporter protein), a structural change of the protein due to binding of a target substance results in a change in the detection signal generated by the reporter protein. The present invention has been accomplished on the basis of these findings.

Namely, according to the present invention, there is provided a sensor protein comprising an insert-type fusion protein composed of a reporter protein and a binding protein wherein said binding protein is inserted into the amino acid sequence of said reporter protein.

Preferably, the binding protein is a protein having a size of 100 to 1000 amino acid residues in length.

Preferably, the binding protein is a protein selected from the group consisting of metal ion-binding proteins, DNA-binding proteins, cAMP-dependent protein kinase, cGMP-dependent protein kinase, hydrolase, ATP-binding proteins, GTP-binding proteins, nitric monoxide synthase, glucose-binding proteins, maltose-binding proteins, hormone receptors, single chain antibodies and chaperons, or a functional fragment thereof or a mutant thereof.

Preferably, the reporter protein is an enzyme protein, a fluorescent protein or a fluorescence-labeled protein, or a mutant thereof.

Preferably, the enzyme protein is an enzyme protein selected from the group consisting of protease, nuclease, alkaline phosphatase, β-galactosidase, luciferase, glucose oxidase, chloramphenicol acetyl transferase and peroxidase; or a mutant thereof.

Preferably, the fluorescent protein is Green Fluorescent Protein, Red Fluorescent Protein or a mutant thereof.

Preferably, the binding protein is inserted between the amino acid residues of 128 Ile-205 Ser of Green Fluorescent Protein which is the reporter protein.

Preferably, the fluorescent-labeled protein is a protein labeled with a fluorescent dye selected from fluorescein series, rhodamine series, eosin series and 7-nitrobenz-2-oxa-1,3-diazole (NBD) series, or a mutant thereof.

Preferably, the sensor protein of the present invention is comprised of an insert-type fusion protein formed by inserting the amino acid sequence of aryl hydrocarbon (Ah) receptor into the amino acid sequence of alkaline phosphatase.

According to another aspect of the present invention, there is provided a nucleic acid encoding the protein of the present invention.

According to still another aspect of the present invention, there is provided a method of preparing a sensor protein, comprising the steps of:

(a) inserting a DNA encoding a binding protein into a DNA sequence encoding a reporter protein; and (b) expressing the resultant DNA encoding an insert-type fusion protein.

According to still further aspect of the present invention, there is provided a method of preparing a sensor protein, comprising the steps of:

(a) inserting a DNA encoding a binding protein into a DNA sequence encoding a reporter protein;

(b) introducing mutation into the resultant DNA sequence encoding an insert-type fusion protein to obtain a population of mutants of the DNA sequence encoding the insert-type fusion protein;

(c) expressing the population of mutants of the DNA sequence encoding the insert-type fusion protein to obtain a population of mutants of the insert-type fusion protein; and (d) selecting an insert-type fusion protein having a desired function from the population of mutants of the insert-type fusion protein by detecting a change in the detection signal generated from the reporter protein by the action of a target substance to the binding protein.

Preferably, the steps (b), (c) and (d) are repeatedly carried out.

According to still further aspect of the present invention, there are provided a sensor protein obtained by the above-mentioned method of the present invention, and a nucleic acid encoding said sensor protein.

According to still further aspect of the present invention, there are provided an expression vector containing said nucleic acid of the present invention, and a transformed cell having said expression vector.

According to still further aspect of the present invention, there is provided a method of preparing a sensor protein, comprising the steps of:

culturing the transformed cell of the present invention; and harvesting a sensor protein from the culture.

According to still further aspect of the present invention, there is provided a method of detecting or quantifying a target substance comprising the steps of:

reacting the sensor protein of the present invention with an a target substance; and measuring a change in the detection signal generated from the reporter protein that constitutes the sensor protein.

Preferably, the reporter protein is a fluorescent protein. Preferably, the detection signal is fluorescence. Preferably, the detection or quantification is carried out in a living cell, tissue or individual. In a preferred embodiment, the sensor protein is an insert-type fusion protein formed by inserting the amino acid sequence of Ah receptor into the amino acid sequence of alkaline phosphatase, and the target substance is dioxins or polychlorinated biphenyl. In another preferred embodiment, the sensor protein is an insert-type fusion protein formed by inserting the amino acid sequence of calmodulin into the amino acid sequence of a fluorescent protein, and the target substance is a calcium ion. In a still further another preferred embodiment, the sensor protein is an insert-type fusion protein formed by inserting the amino acid sequence of a single chain antibody into the amino acid sequence of alkaline phosphatase, and the target substance is an antigen.

According to a still further aspect of the present invention, there is provided a reagent kit for performing the above method of detection or quantification, which comprises the above-mentioned sensor protein or nucleic acid of the present invention.

BEST MODE FOR CARRYING OUT THE INVENTION

The terms used in the present specification have the following meanings, unless otherwise specified.

The term "sensor protein" means a protein that has both the ability of specifically recognizing a target substance and the ability of generating a signal which can be measured from outside, and shows a change in the signal depending on the specific action (i.e., a specific binding, interaction or the like) of a particular target substance. The change in signal can be detected from the outside, and can be measured physicochemically or the like. This specific "binding or interaction" between a target substance and a sensor protein may also be simply referred to as "a reaction".

The term "reporter protein" means a protein that has the ability of generating a signal which can be measured from outside. In general, the signal is a physicochemically measurable signal.

The term "binding protein" means a protein that has the ability of specifically recognizing a target substance. The "ability of specifically recognizing a target substance" means the ability of giving some change in the structural stability of said protein by a specific action with a target substance (i.e. a specific binding, interaction or the like).

The term "target substance (analyte)" means a molecule or ion which specifically acts on the binding protein and means a substance to be subjected to the detection or quantification by the use of the sensor protein of the present invention.

The term "nucleic acid" means DNA or RNA, or derivatives thereof.

Figure 1:
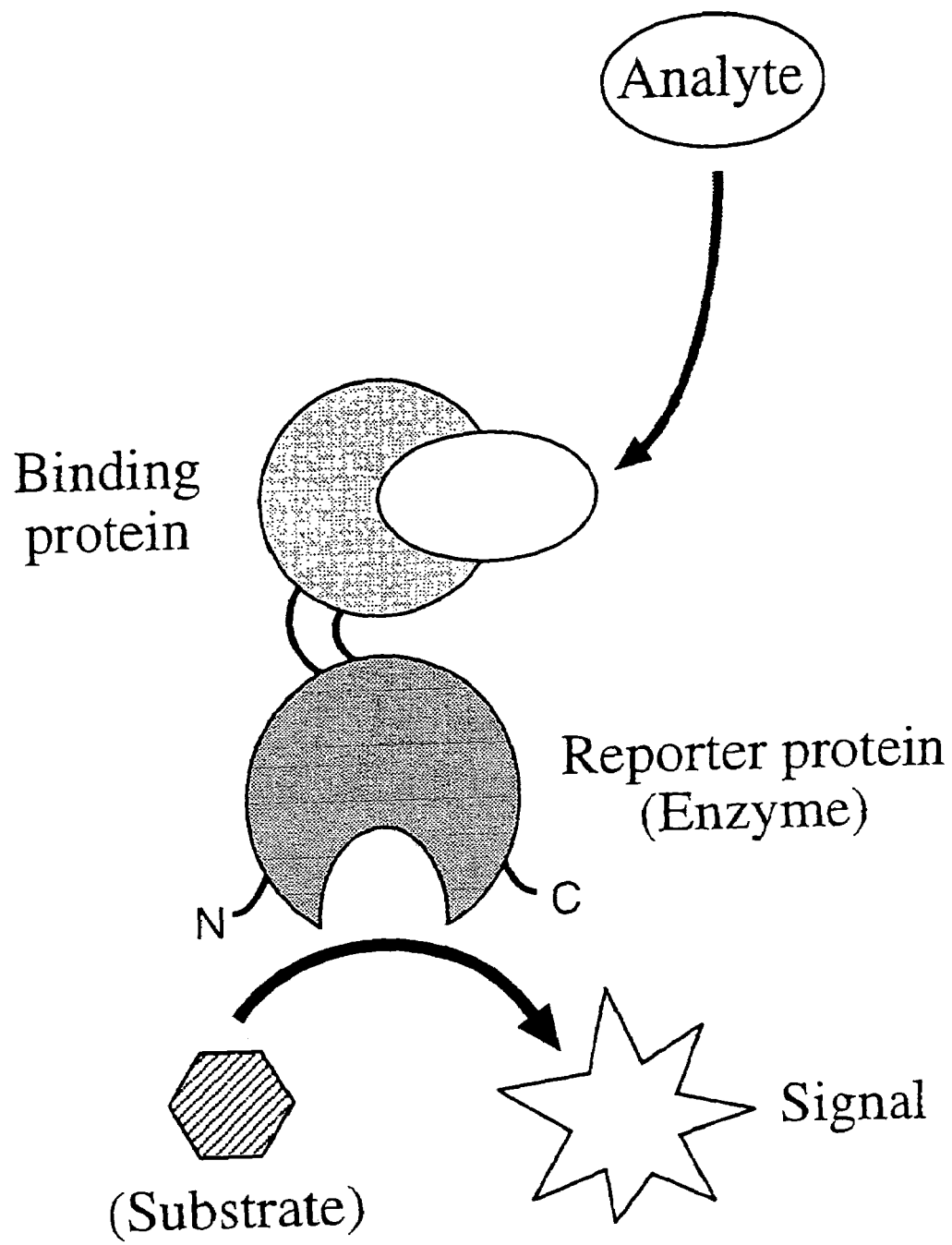
FIG. 1 is a conceptional diagram showing the detection of a target substance by the use of the sensor protein of the present invention. The sensor protein of the present invention has a structure where a binding protein is inserted into a reporter protein. When the structure of the protein is changed by binding or interaction of a target substance with a binding protein, detection signal generated from the reporter protein is changed.

The sensor protein of the present invention comprises an insert-type fusion protein that can be obtained by inserting a binding protein for recognizing a target substance into the amino acid sequence of a reporter protein capable of generating a signal, and the signal generated by the reporter protein part can be changed by the binding of the target substance or the interaction therewith (see FIG. 1).

"A binding protein is inserted into the amino acid sequence of a reporter protein" means a state wherein the binding protein is inserted into the amino acid sequence of the reporter protein thereby the reporter protein is divided into two sections by the binding protein and at least one amino acid residue of the reporter protein remains on each side of N-terminus and C-terminus of the binding protein after the insertion. In the sensor protein of the present invention, the binding protein is inserted into the amino acid sequence of the reporter protein at such a position that the capability of generating a signal which the reporter protein inherently possesses is not lost.

Specifically, the reporter protein, which is one component of the sensor protein of the present invention, includes enzyme proteins, fluorescent proteins, fluorescent substance-labeled proteins and the like.

More specifically, the enzyme protein is not specifically limited so long as it is an enzyme capable of binding specifically to a substrate to catalyze the reaction. Examples thereof include proteases, nucleases, alkaline phosphatase, β-galactosidase, luciferase, glucose oxidase, chloramphenicol acetyl transferase (CAT), peroxidase and the like, and mutants thereof are also included. Methods of generating a mutant and screening thereof will be described below. A change of a substrate such as decomposition or modification by the enzyme activity can be detected as a physicochemical signal.

Further, in a fluorescent protein containing an endogenous fluorescent chromophore or a protein labeled with an exogenous fluorescent chromophore via a covalent or non-covalent bond, the fluorescence of the chromophore is sensitively changed depending on the ambient environment, so that the change can be detected by a physiological method. Specifically, the fluorescent protein includes, for example, Green Fluorescent Protein (GFP), and Red Fluorescent Protein (RFP) and its mutant. The protein labeled with an exogenous fluorescent substance (fluorescence-labeled protein) includes a protein labeled with a fluorescent dye such as fluorescein series, rhodamine series, eosin series, 7-nitrobenz-2-oxa-1,3-diazole (NBD) series. A protein can be labeled with a fluorescent dye by a method in which the protein is labeled with a fluorescent dye via a non-covalent bond, such as a method of modifying hem of hemoglobin with a fluorescent dye; or by a method in which the protein is labeled with a fluorescent dye via a covalent bond, such as a method of chemically modifying a cysteine residue of the protein with a fluorescent dye. While the type of the protein to be labeled with an exogenous fluorescent substance are not limited, for example, thioredoxin which is easily expressed in a large scale in *E. coli*, glutathione-S-transferase (GST) which adsorbs into an affinity resin, cellulose-binding domain or the like are labeled with a fluorescent dye, and are used as a reporter protein, and these are particularly advantageous for synthesis and purification of the sensor protein in a large scale.

Further, the binding protein that is another component of the sensor protein of the present invention is a protein having the ability of specifically recognizing a target substance. Specifically, the binding protein includes, for example, metal ion-binding proteins such as calmodulin or zinc finger domain; DNA-binding proteins such as transcription factors; cAMP-dependent protein kinase; cGMP-dependent protein kinase; hydrolases; ATP-binding proteins; GTP-binding proteins; nitric monoxide synthase; glucose-binding proteins; maltose-binding proteins; hormone receptors such as aryl hydrocarbon (Ah) receptor and estrogen receptor; single chain antibodies (scFv); and chaperons. In the present invention, functional fragments of the above proteins may be used as a binding protein. The term "a functional fragment of a protein" in the present specification is a protein which consists of a partial fragment of the above-mentioned specific protein and still maintains the ability of specifically recognizing a target substance. Further, in the present invention, mutants of the above-mentioned proteins may be used. A method of preparing and screening a mutant will be described below. The size of the binding protein or the like is not particularly limited, and a protein of about 100 to 1000 amino acid residues is preferred.

The target substance (analyte) to be detected by the sensor protein of the present invention is not particularly limited so long as it can specifically bind to or interact with the binding protein. Specific examples includes metal ions such as calcium and zinc ions; nucleic acid derivatives such as cAMP, cGMP, ATP and GTP; low molecular weight compounds such as nitric monoxide; sugars such as glucose and maltose; chemical substance such as dioxins and polychlorinated biphenyl (PCB); hormones, antigens, proteins, nucleic acids, viruses, cells and the like. The dioxins include polychlorinated paradioxins (PCDD) and polychlorinated dibenzofurans (PCDF), and there are 210 types of homologues and isomers in total. Further, the polychlorinated biphenyl (PCB) includes 209 types of homologue and isomers, and among these, 13 types of coplanar PCB isomers having a planar structures are known as highly toxic compounds.

In the insert-type fusion protein of the sensor protein of the present invention, a site where the binding protein is inserted into the reporter protein is not particularly limited. Specifically, it is a site that is exposed to the surface of the reporter protein in the structure of the reporter protein, and more preferably a vicinity of the reporter site which generates a signal or a site suitable to appropriately destabilize the structure of the reporter protein by the insertion. When the reporter protein is, for example, GFP, the site where the binding protein is inserted is preferably between the amino acid residues of 128 Ile-205 Ser, and more preferably between the amino acid residues of either 171 Ile-175 Ser or 140 Lys-145 Asn.

In the sensor protein comprised of the above-mentioned structure according to the present invention, the reporter protein becomes highly sensitive to a change in the structural stability or conformation by inserting the binding protein into the amino acid sequence thereof, and the detection signal based on enzyme activity or fluorescence thereof is changed by binding of the target substance to the binding protein. This "change in a detection signal" includes an increase/decrease in signal "intensity" as well as a change in signal "property". Specifically, it includes an increase/decrease of absorbance or fluorescence intensity as well as the shift of fluorescence wavelength. The greater such a change of signal is, the more preferred it is in the present invention. Therefore, it is preferred to further introduce a mutation to the insert-type fusion protein by a method described below and to obtain mutants capable of providing a greater change in signal by screening.

The sensor protein of the present invention can be synthesized by any technique for synthesis of proteins, such as recombinant genetic engineering, chemical synthesis or cell-free translation.

For example, the DNA sequence encoding the binding protein is inserted into the DNA sequence encoding the reporter protein which constitutes the sensor protein of the present invention to construct the DNA encoding an insert-type fusion protein. The resultant DNA is inserted into an expression vector containing a promoter, a terminator and the like in such a manner that the DNA can be expressed to obtain an expression vector. A suitable host cell is transformed with the thus-formed vector and the transformed cell is cultured, whereby the sensor protein of the present invention can be prepared.

Namely, the DNA encoding the reporter protein is cut with a suitable restriction enzyme and then, the DNA encoding the binding protein, which has two ends which can be linked with the two DNA fragments obtained by the cutting, is linked with the two cut ends of the DNA encoding the reporter protein, whereby the DNA encoding the binding protein is inserted into the DNA sequence encoding the reporter protein so as to construct the DNA encoding an insert-type fusion protein. Further, the desired two DNA fragments encoding the N-terminus side portion and C-terminus side portion of the reporter protein can be synthesized from the genetic DNA encoding the reporter protein by a PCR method using suitable plural primers.

Two fragments of the DNA encoding a reporter protein can be synthesized by inserting a proper restriction enzyme site into the DNA encoding the reporter protein by a PCR method using a primer having a proper sequence and cutting the resultant DNA encoding the reporter protein in the above manner. The thus-obtained two fragments of the DNA encoding the reporter protein and the DNA fragment encoding a binding protein are linked in accordance with a usual method using a ligase, whereby a DNA fragment encoding the sensor protein of the present invention, which has a desired sequence, can be obtained.

As the expression vector containing the DNA sequence encoding the sensor protein of the present invention, any vector can be used so long as it can express the DNA sequence. In general, the vector contains a promoter, a transcriptional region composed of the DNA encoding the protein of the present invention, signal sequences for starting and terminating transcription, and it may further contain expression control regions such as a repressor binding site and an enhancer and a base sequence such as a selection marker.

The promoter which can be used in the expression vector of the present invention includes, for example, phage λPL, T7, T3 and SP6 promoters; lac, trp, lpp, tac and BAD promoters of *E. coli*; SPO1 promoter, penP promoter of *bacillus* bacterial; pho5 promoter, PGK promoter, GAP promoter, ADH1 promoter, SUC2 promoter, GAL4 promoter, Mfα promoter of yeast; polyhedron promoter, P10 promoter of insect cell; SV40 early and late promoters of animal cells; retrovirus LTR promoter, CMV promoter, HSV-TK promoter, metallothionein promoter; 35S promoter for plant cells; a promoter of rice actin gene and the like.

The selection marker suitable for use in the expression vector of the present invention includes, for example, a dihydrofolic acid reductase (dhfr) gene, a neomycin resistance gene for eukaryotic cells, and a tetracycline or ampicillin resistance gene for bacteria. The dhfr gene confers methotrexate resistance to the transformed cell, and the neomycin gene confers G418 resistance to the transformed cell. When a host is a dhfr gene-defective CHO cell and the dhfr gene is used as the selection marker, it is possible to select the transformant in a thymidine-free culture medium. In this case, cultivation is carried out while gradually increasing methotrexate (MTX) concentration, to select resistant strains, thereby the DNA sequence encoding the sensor protein of the present invention is amplified in the resistant cell together with the dhfr gene, and a CHO (dhfr-) cell of high level expression can be obtained.

If necessary, the above-mentioned expression vector may be constructed in such a way that a signal sequence is added to the N-terminus of the protein. Such a signal sequence is PhoA signal sequence, SUC2 signal sequence or the like for *E. coli* host, and it is Mfαsignal sequence, SUC2 signal sequence or the like for yeast host, and it is α-interferon signal sequence or the like for animal cell host.

The host cell in which the DNA sequence encoding the sensor protein of the present invention is expressed includes eukaryotic cells such as mammalian cells, plant cells, insect cells, yeast and *aspergillus*; and prokaryotic cells such as bacterial cells. Mammalian cells, yeast and bacterial cells are preferred. The above expression vector is introduced into a host cell by calcium phosphate transfection, electroporation, transduction, infection or other method. The sensor protein of the present invention can be expressed in the above-mentioned eukaryotic or prokaryotic host cells under the control of the above promoter.

The prokaryotic cell which can be used as the host includes, for example, *E. coli, Bacillus subtilis, Salmonella, Pseudomonas, Streptomyces, Staphylococcus* and the like. Yeasts includes, for example, *Saccharomyces cerevisaie, Schizosaccharomyces pombe, Pichia pastoris* and the like. Mammalian cells includes, for example, COS cell, mouse AtT-20 cell, rat GH3 cell, rat MtT cell, mouse MIN6 cell, Vero cell, C127 cell, CHO cell, dhfr gene-defective CHO cell, HeLa cell, L cell, BHK cell, BALB 3T3 cell, 293 cell, Bows melanocyte and the like.

The sensor protein of the present invention can be expressed by culturing the prokaryotic cell transformed by the above expression vector in a liquid medium containing a carbon source (e.g., glucose, dextran, soluble starch, etc.), a nitrogen source (e.g., an ammonium salt, a nitric acid salt, peptone, casein, meat extract, bean cake, etc.) and an inorganic substance (e.g., calcium chloride, sodium dihydrogen phosphate, magnesium chloride, etc.) at an appropriate pH (pH of about 5 to 8) for an appropriate period of time (about 3 to 24 hours). When an expression vector containing an inducible promoter is employed, induction with temperature or a chemical inducing substance is performed, and then the transformed cell is cultured in the same manner as described above, whereby the sensor protein of the present invention can be expressed. The appropriate cultivation temperature is in a range of about 14 to 43° C. in the case of *E. coli* or in a range of about 30 to 40° C. in the case of *Bacillus* bacteria. After the cultivation, the cell is disrupted by a physical or chemical method, and the sensor protein of the present invention is purified from the resultant crude extract. While the sensor protein obtained in the above manner can be purified by a usual method, it is advantageous to produce a sensor protein in which a plurality of histidine residues are added to the N- or C-terminus and to purify the sensor protein by an affinity chromatography. Alternatively, the transformed cell is cultured by a known method when the host is yeast, a mammalian cell, an insect cell or the like, and the produced sensor protein of the present invention may be purified by a known method.

The sensor protein of the present invention can be also synthesized in a cell-free protein synthesis system. The above expression vector DNA is transcribed in vitro, and the resultant mRNA is added to an cell-free translation system to synthesize the protein. Specifically, the cell-free translation system is prepared from an extract of an eukaryotic cell or a bacterial cell, or a portion thereof. As particularly preferred examples, there are cell-free translation system prepared from a rabbit reticulocyte, a wheat germ and an extract of E. coli (E. coli S30 extract). The produced sensor protein of the present invention may be purified by a known method.

The function of the thus-obtained insert-type fusion protein as a sensor can be assessed by detecting a change in a signal generated from the reporter protein upon binding or interacting with a target substance, such a change being, for example, an amount of a change in intensity of fluorescence or shift of fluorescence wavelength when the reporter protein is a fluorescent protein, or an amount of a change in enzyme (catalytic) activity which the reporter protein itself has when the reporter protein is an enzyme. The detection of the change of intensity of fluorescence, the change of fluorescence wavelength, the change of enzyme activity or the like can be carried out by a usual method known per se.

When the insert-type fusion protein obtained by the above method does not function as a sensor or when further improvement of the function as a sensor is desired, an insert-type fusion protein having the desired function can be obtained by introducing a mutation into the DNA sequence encoding the insert-type fusion protein obtained above, expressing the mutant in the same way as above and assessing the function of the resultant protein, and if necessary, repeating these steps. Specifically, a mutation is introduced into the DNA sequence encoding the insert-type fusion protein to prepare a population of mutant DNA sequences, and then, a desired sensor protein which shows a significant change in the signal generated by binding of a target substance may be selected by screening from a population of mutants of the insert-type fusion protein obtained by expressing the population of the mutant DNA sequences.

As a method of introducing a mutation into a DNA sequence, a number of methods are known, and such methods include, for example, a classical method using transposon or a mutagen (Bostein & Shortle 1985. Science 229, 1193–1201), Error-prone PCR (Leung et al. 1989. Technique 1, 11–15), a method of substituting a particular region of a DNA sequence with a random sequence by means of random chemical synthesis of DNA (Zhou et al. 1996. Nature Struct. Biol. 3, 446–451; Axe et al. 1996. Proc. Natl. Acad. Sci. USA 93, 5590–5594), a sexual PCR method (Stemmer 1994. Nature 370, 389–391), a site-directed mutagenesis and the like.

The above recombinant DNA experimental techniques for preparing the sensor protein of the present invention are described in many recombinant experiment manuals (e.g., Molecular Cloning, A Laboratory Manual, 2nd Ed., Sambrook et al., Cold Spring Harbor Laboratory Press, Cold Spring Harbor, N.Y. (1989)), and those skilled in the art can easily carry out not only the techniques but also modified methods thereof.

As described above in detail, the sensor protein of the present invention is a molecular sensor which incorporates specific molecule recognizing mechanisms of various proteins, which mechanism has not been usable heretofore. The present invention provides a general method for designing and screening such a molecular sensor as required. By using the sensor protein of the present invention, it becomes possible to detect a particular molecule, ion or the like contained in a solution. The sensor protein is widely applied and can be utilized in various fields such as cell biology, environment, bio-computer, biomedicine and other fields. Particularly, it can be suitably used for detection or quantification of endocrine disrupting chemicals, a fluorescent molecule imaging in a living cell, simple measuring methods of an antigen-antibody reaction and the like. The outline of application examples of the sensor protein of the present invention will be described below:

(1) Detection or Quantification of Endocrine Disrupting Chemicals

Recently, it has been revealed that a number of chemical substances having conferred a large benefit on human being in accordance with development of chemical industries have the negative side that they act on natural animate beings as endocrine disrupting chemicals, which is one of the serious issues which human being in the 21st century have to solve. In order to overcome the problem, it is urgently required to develop a simple method of detection or quantification of endocrine disrupting chemicals, which enables large scale screening, for the purpose of assessing a chemical substance that may disrupt endocrine system or for the purpose of investigation of actual conditions with respect to the effect of a chemical substance in the natural world. As is described in detail in Example 3 below, it becomes possible to simply detect or quantify a chemical substance that acts as endocrine disrupting chemicals, or vitellogenin or the like which are derived in fish by endocrine disrupting chemicals, by means of the sensor protein obtained by inserting Ah receptor, estrogen receptor, anti-vitellogenin antibody or the like into an enzyme such as alkaline phosphatase or β-galactosidase or a fluorescent protein and making a selection after subjecting the proteins to mutagenesis.

(2) Fluorescent Molecule Imaging in Living Cell

Figure 7:
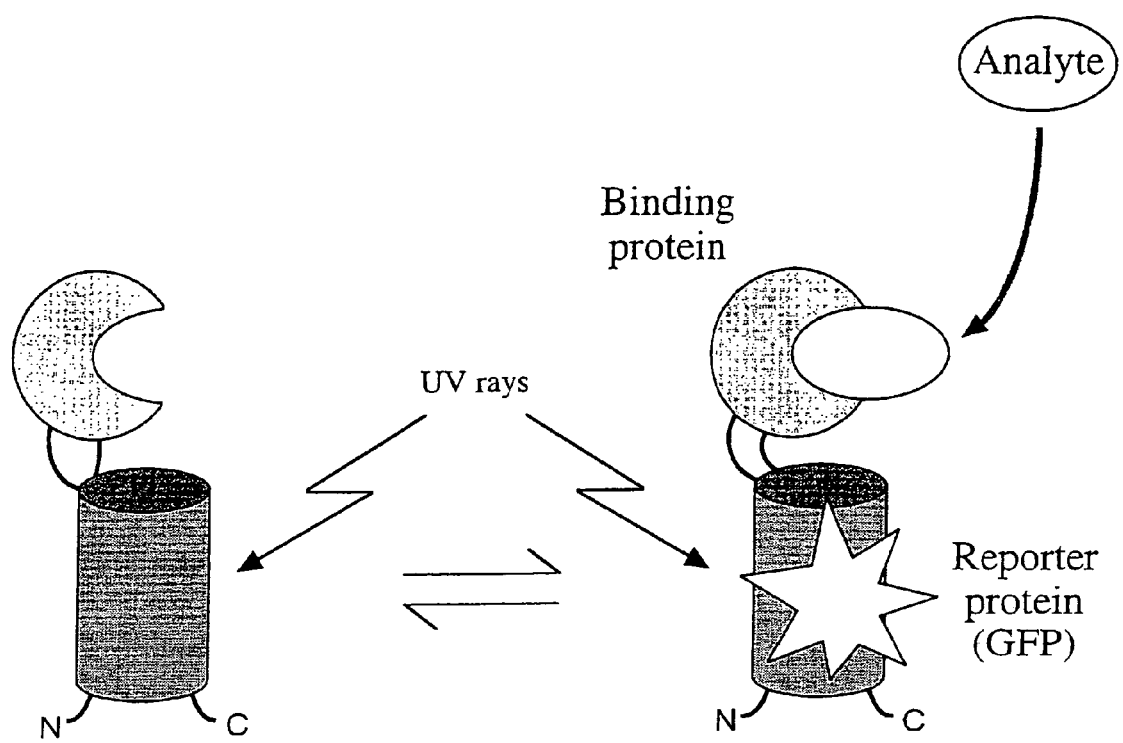
FIG. 7 is a conceptual diagram showing one embodiment of utilization of the sensor protein of the present invention, particularly, showing a light sensor protein that is formed by inserting any binding protein into a fluorescent protein (as a reporter protein; GFP), and shows a change in the fluorescence by stabilization of the structure due to the binding of a target substance.

In order to understand complicated life phenomena such as development and differentiation, immunization and signal transduction, fluorescent imaging techniques for monitoring the operation of a particular molecule in a cell become popular recently. As an application example of the sensor protein of the present invention, there can be mentioned a light sensor protein which is obtained by inserting any binding protein into a fluorescent protein that is a reporter protein, and shows a change in fluorescence due to stabilization of the structure by the binding of a target substance (see FIG. 7). Specifically, by using the sensor protein obtained by inserting calmodulin, cAMP-dependent protein kinase, nitric monoxide synthetase or the like into a fluorescent protein such as GFP and making a selection after subjecting the proteins to mutagenesis, it becomes possible to trace, in the living cell, the distribution, concentration or the like of molecules which play an important role in a living body, such as a metal ion (e.g. calcium or the like), cAMP or nitric monoxide. Such a molecular-recognizing GFP sensor can be utilized in any cells to which a gene can be transferred, since it binds to a target substance to generate fluorescence by only expressing the gene in a cell.

Further, the molecular-recognizing GFP sensor can be utilized as an element of a bio-computer. While bacteriorhodopsin, which is presently expected to be an element of a bio-computer, is an element that recognizes light to convert it into molecular information (Birge 1995. Sci. Am. 272, 66–71), the molecular-recognizing GFP sensor is expected to play a complimentary role as an element that recognizes a particular molecule to convert it into light information.

(3) Simple Method of Measuring Antigen-Antibody Reaction

For example, by using the sensor protein obtained by inserting a single chain antibody (scFv) as a binding protein into an enzyme such as β-galactosidase, and making a selection after subjecting the protein to mutagenesis, an antigen-antibody reaction can be more simply measured than in conventional enzyme-linked immunosorbent assay (ELISA). While the conventional enzyme-linked immunosorbent assay (ELISA) requires 6 steps consisting of immobilization of an antibody onto a solid phase, blocking, an antigen-antibody reaction, a reaction with a secondary antibody, an enzyme reaction, and detection or quantification, the measuring method using the sensor protein of the present invention requires only 3 steps of an antigen-antibody reaction, an enzyme reaction and detection or quantification, so that the latter makes it possible to measure a target substance with a smaller labor for a short period of time. Furthermore, by using the sensor protein constructed by inserting the above antibody into a fluorescent protein, it is possible to detect or quantify an antigen-antibody reaction as a change in fluorescence, so that a target substance can be more simply measured.

The reagent kit for performing detection or quantification and imaging a target substance with the sensor protein of the present invention as mentioned above can be prepared by any method known per se.

EXAMPLES

The present invention will be described more in detail below with reference to Reference Examples and Examples. However, Examples described below are provided by way of only explanation of the present invention, and the scope of the present invention is by no means restricted by the following Examples. It is apparent for those skilled in the art that any alteration, improvement or modification can be applied to the present invention without departing from the spirit of the present invention.

In the following Reference Examples and Examples, basic operations of gene engineering (e.g., cloning, transformation and cultivation of E. coli, collection of plasmids and the like) were carried out according to the experimental manual of Molecular Cloning, A Laboratory Manual, 2nd Ed., Sambrook et al., Cold Spring Harbor Laboratory Press, Cold Spring Harbor, N.Y. (1989).

Reference Examples 1 and 2

Demonstration that a Binding Protein Can be Inserted into a Reporter Protein

For attaining the construction of the sensor protein of the present invention with various combinations of a binding protein and a reporter protein, it is first required to satisfy the condition that when any binding protein is inserted into any reporter protein, the ability of generating a signal is not lost. Although the experiments of inserting a foreign amino acid sequence into a protein have been carried out for a long time, the sequence to be inserted has been limited to the length of about 20 amino acid residues at most. However, the present inventors recently reported that even when a protein composed of 120 amino acid residues having an arbitrary sequence was inserted into ribonuclease H which was an enzyme protein, an insert-type fusion protein still maintaining the enzyme activity could be obtained with high frequency (Doi et al. 1997. FEBS Lett. 402, 177–180). Then, in order to demonstrate that any other reporter proteins permit the insertion of such a long amino acid sequence, a random sequence composed of 120 amino acid residues was inserted into kanamycin nucleotidyltransferase (KNTase) which is an enzyme protein and GFP which is a fluorescent protein, respectively, and it has been confirmed as follows that the enzyme activity and the fluorescence are maintained.

1. Insertion of Random Sequence of 120 Amino Acid Residues into KNTase

A random sequence of 120 amino acid residues was inserted into kanamycin nucleotidyltransferase (KNTase) which is an enzyme protein having 253 amino acid residues, and presence/absence of the enzyme activity was examined by observing, as an indicator, the growth of E. coli capable of expressing the resultant insert-type fusion protein on a medium containing kanamycin.

Experimental Materials

E. coli JM109 strain and plasmids pUC18 and pBEST501 (Itaya et al. 1989. Nucleic Acids Res. 17, 4410) were provided by Dr. Itaya of Mitsubishi Chemical Corporation, Institute of Life Science. Plasmid library R1MIX (Prijambada et al. 1996. FEBS Lett. 382, 21–25) was provided by Dr. Yomo of Osaka University.

Commercially available enzymes and reagents were used respectively as follows:

Restriction enzyme KpnI (NEB), EcoRI and PstI (Toyobo Co., Ltd.), HindIII and SalI (Boehringer Mannheim); gene kit Ligation High and Blunting High (Toyobo Co., Ltd.); heat-stable enzyme Vent DNA Polymerase (NEB); and ampicillin and kanamycin (Wako Pure Chemical Industries, Ltd.).

Construction of Plasmid

A plasmid pUC-Kn was constructed in accordance with the following procedure. First, a plasmid pUC18 was digested by HindIII to delete the HindIII site, and was treated to make an blunt end and then, it was self-cyclized to obtain a plasmid pUC18ΔH. On the other hand, for introducing a restriction enzyme site for insertion of a random sequence into a KNTase gene, DNA fragments of the N- and C-terminus of the KNTase were amplified by PCR using pBEST501 as a template and two sets of primers, each of the DNA fragments was digested by PstI-SalI or SalI-EcoRI, and both of the thus-digested DNA fragments were inserted at once into the PstI -EcoRI site of the pUC18ΔH. As the result, a plasmid pUC-Kn was obtained in which a HindIII-SalI-KpnI site was introduced between 126 Val and 127 Glu of-KNTase.

Insertion of Protein Composed of Random Amino Acid Sequence and Screening

Random regions of the plasmid library R1MIX containing a random amino acid sequence were amplified by PCR using primers, and digested by HindIII-KpnI and inserted into HindIII-KpnI site of KNTase gene on the pUC-Kn. The resultant DNA library was introduced into E. coli JM109 strain, and the E. coli was cultured on an LB plate containing 100 μg/ml of ampicillin and 0 to 50 μg/ml of a kanamycin concentration gradient to allow the E. coli to form colonies. Then, a number of E. coli colonies that could grow under the kanamycin concentration of 10 μg/ml were obtained. It was therefore demonstrated that regardless of the sequence to be inserted, a protein having 100 or more amino acid residues in length could be inserted into KNTase without losing the enzyme activity of KNTase.

2. Insertion of Random Sequence of 120 Amino Acid Residues into GFP

The presence/absence of fluorescence was examined by detecting, as an indicator, the green fluorescence generated under ultraviolet light by the E. coli which expressed the insert-type fusion protein obtained by inserting a random sequence of 120 amino acid residues into a fluorescent protein, GFP.

A random sequence of 120 amino acid residues was inserted into the loop site between 172 Gln and 173 Asp of GFP in the same manner as in the above 1. The DNA prepared by inserting the random sequence into the GFP gene encoded on the pND101 described in detail in Example 1 below, was introduced into E. coli JM109, and the grown colonies were observed under ultraviolet light. The green fluorescence was maintained though its intensity was approximately 10% of that of the wild type GFP. It was therefore demonstrated that regardless of the sequence to be inserted, a protein of 100 or more amino acid residues in length could be inserted into GFP without losing the fluorescence of GFP.

Example 1

In Vivo Screening of Sensor Protein

In this experiment, β-lactamase was selected as one example of the binding protein. The X-ray crystallographic structure of sole β-lactamase as well as that of the complex of β-lactamase and β-Lactamase Inhibitory Protein (BLIP) have been determined. It is known that the structure of β-lactamase is hardly changed by binding of BLIP (Strynadka et al. 1996. Nature Struct. Biol. 3, 290–297). Therefore, if a sensor protein can be constructed by the use of β-lactamase as the binding protein, it is possible to demonstrate that the sensor protein can be constructed according to the method of the present invention even by the use of proteins other than those used in the conventional sensor proteins, which undergo a drastic change of the structure by binding of the substrate.

As the reporter protein into which β-lactamase was inserted, green fluorescence protein (GFP) was selected. GFP has a fluorescent chromophore in its insides and generates green fluorescence under ultraviolet light. First, an insert-type fusion protein was constructed by inserting β-lactamase into the loop site between 172 Gln and 173 Asp of GFP. Further, a sensor protein wherein the fluorescent intensity of GFP was increased by binding of BLIP was selected from the library of insert-type fusion proteins obtained by introducing a random mutation into the insert-type fusion protein obtained above.

Experimental Materials

E. coli JM109, and plasmids pUC18 and pUC4KIXX (Barany 1985. Gene 37, 111–123) and pGFPuv (Crameri et al. 1996. Nature Biotechnol. 14, 315–319) were provided by Dr. Itaya of Mitsubishi Chemical Corporation, Institute of Life Science. Plasmid pEOR (Prijambada et al. 1996. FEBS Lett. 382, 21–25) was provided by Dr. Yomo of Osaka University and BLIP gene (Doran et al. 1990. J. Bacteriol. 172, 4909–4918) was provided by Dr. Schroeder of Alberta University (Canada).

The following commercially available enzymes and reagents were used respectively:

Restriction enzymes AflIII, BspHI, KpnI, NcoI, NdeI, NheI and XbaI (NEB), Eco47III and EcoRI (Toyobo Co., Ltd.), HindIII and SacI (Boehringer Mannheim), and XhoI (Takara Shuzo Co., Ltd.); gene kits Ligation High and Blunting High (Toyobo Co., Ltd.); heat-resistance enzymes Taq DNA Polymerase (Grainer) and Vent DNA Polymerase (NEB); and carbenicillin (Sigma), and kanamycin, L-arabinose and D-glucose (Wako Pure Chemical Industries., Ltd.).

Construction of Plasmid

Figure 2:
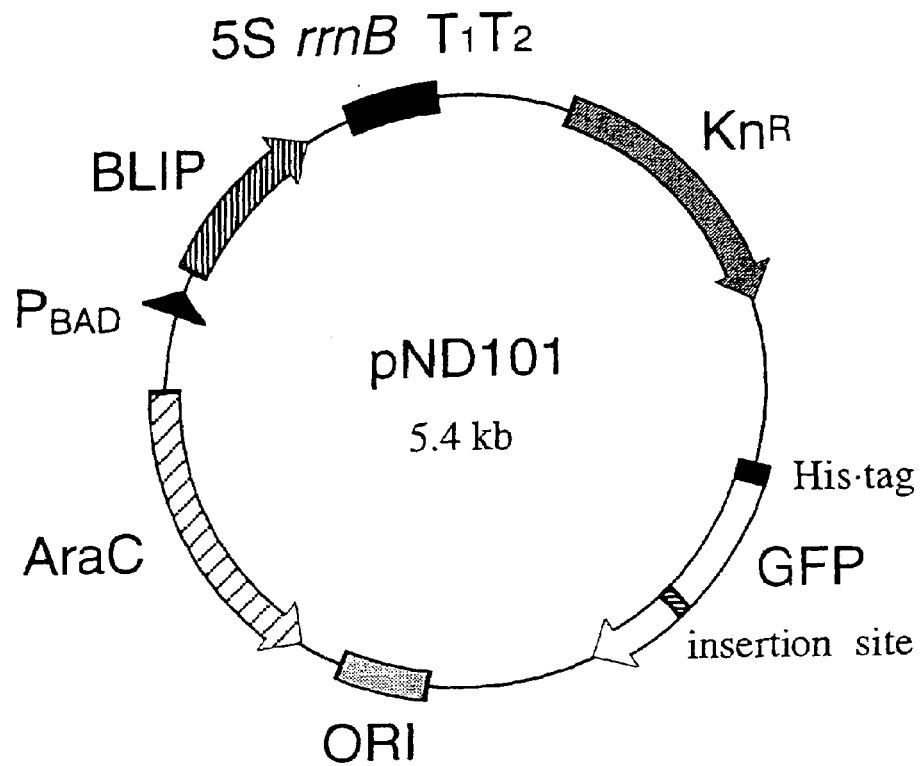
FIG. 2 is a diagram showing the gene map of vector pND101 used for screening and large scale expression of a sensor protein. Expression of BLIP gene contained in the above vector is induced in the presence of L-arabinose and suppressed in the presence of D-glucose, by a regulator AraC of BAD promoter. GFP gene contains a restriction enzyme site where β-lactamase gene is to be inserted.

The plasmid pND101 (as shown in FIG. 2) was constructed in accordance with the following procedure. First, BAD promoter and AraC protein gene that controls the expression of a gene under BAD promoter (Guzman et al. 1995. J. Bacteriol. 177, 4121–4130) were amplified by PCR using the genome of E. coli JM109 strain as the template and primers (Sequence Nos. 1 and 2), digested with NcoI and NdeI and cloned in AflIII-NdeI site of pEOR. Then, the resultant plasmid was digested with BspHI to delete ampicillin-resistant gene which was substituted with kanamycin-resistant gene contained in the AflIII-XhoI fragment of pUC4KIXX. Further, PCR fragments obtained by amplifying BLIP gene with primers (Sequence Nos. 3 and 4) were digested with NdeI and SacI, and inserted into the downstream of BAD promoter. By this procedure, the expression of BLIP can be induced in the presence of L-arabinose and suppressed in the presence of D-glucose. The resultant plasmid was digested with SacI and HindIII to delete its HindIII site, and treated to make blunt ends, and then it was self-cyclized to obtain a plasmid pBAD-BLIP-Kn.

On the other hand, in order to introduce a restriction enzyme site for inserting β-lactamase gene into GFP gene, DNA fragments of the N- and C-terminus of GFP were amplified by PCR using pGFPuv as a template and two sets of primers (Sequence Nos. 5 and 6, and Sequence Nos. 7 and 8), and each of the DNA fragments was digested with NheI-KpnI or KpnI-SacI respectively, and the DNA fragment thus digested were inserted at once into the NheI-SacI site of pEOR. As the result, a HindIII-KpnI-EcoRI site was inserted between the 172 Gln and 173 Asp of GFP and at the same time, a sequence encoding 6 histidine residues was added at the N-terminus of GFP. The thus-obtained mutant GFP gene was amplified by PCR using primers (Sequence Nos. 8 and 9) and inserted into Eco47III site of the pBAD-BLIP-Kn. At this time, in order to bring an expression amount of the mutant GFP to the same level as that of BLIP located in the downstream of BAD promoter, the 6 bases corresponding to −35 region of tac promoter contained in the primer (Sequence No. 9) were made to be random, and a pND101 was finally obtained by selecting one which contained a promoter having the same strength level as BAD promoter.

Insertion of Binding Protein and Screening

Figure 3:
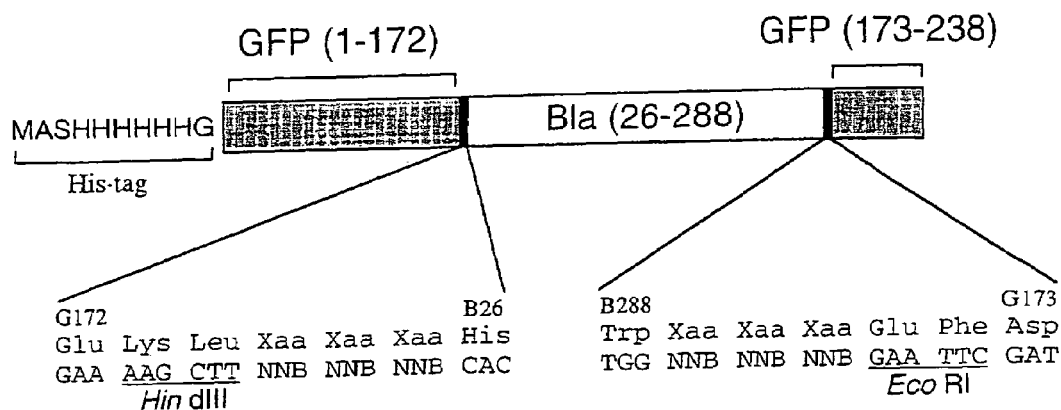
FIG. 3 is a diagram showing construction of a DNA sequence which shows the insertion of β-lactamase gene [Bla (26–288)] into the base sequence of GFP gene. Each linker positioned at both ends of β-lactamase contains a restriction enzyme site of 6 bases and a random sequence of 9 bases.

The β-lactamase gene on the pUC18 was amplified with primers (Sequence Nos. 10 and 11), digested with HindIII-EcoRI and inserted into the HindIII-EcoRI site of GFP gene on the pND101 (FIG. 3). Each of these primers contains a random sequence consisting of 9 bases as a linker between β-lactamase gene and GFP gene. This DNA library was transferred to E. coli JM109, and the E. coli was cultured on a LB plate containing 10 μg/ml of kanamycin to allow the E. coli to form a colony. 100 colonies were arbitrarily selected and each of the colonies was plated on two plates, each of which contains 0.2% L-arabinose or 0.2% D-glucose respectively, to allow the E. coli to again form a colony, and a colony wherein the intensity of fluorescent generated under ultraviolet light is different between the two plates, was selected. The selected colony was cultured in a liquid medium, plasmids were collected and Error-prone PCR (Buchholz et al. 1998. Nature Biotechnol. 16, 657–662) was carried out by using the thus collected plasmids as a template and primers (Sequence Nos. 12 and 8) to introduce a random mutation into the region containing β-lactamase. The resultant PCR fragment was digested with XhoI and XbaI and inserted into the same site of the original plasmid to form a library of plasmids, and clones which indicated a larger difference in the intensity of fluorescence was selected from the library. These steps of random mutation introduction and selection were repeated two times. The finally obtained *E. coli* containing a sensor protein indicated weak fluorescence when no BLIP was not coexpressed (i.e. on the plate containing glucose) but indicated strong fluorescence when BLIP was coexpressed (i.e. on the plate containing arabinose). Namely, a sensor protein that showed an increase of the fluorescent intensity by binding with BLIP in the cell was obtained.

Example 2

In Vitro Experiment Using Sensor Protein

For confirming that the sensor protein obtained in the above Example 1 by inserting β-lactamase into GFP can actually act as a sensor to BLIP in vitro, the sensor protein and BLIP were purified, fluorescence spectrum of the sensor protein was measured and its dependency on BLIP concentration was examined.

Experimental Materials

Urea (Wako Pure Chemical Industries, Ltd.), IPTG (Nacali Tesque, Inc.) and Ni-NTA resin (QIAGEN) were used, and *E. coli*, plasmids, enzymes and the like as described in the Example 1 were used.

Purification of Sensor Protein and BLIP

*E. coli* JM109 having the plasmid encoding the sensor protein was cultured in a 2xYT medium containing 20 μg/ml of kanamycin at 37° C. until the absorbance at 600 nm became 0.6, and then, IPTG was added thereto in a final concentration of 1 mM and cultivation was continued further for 5 hours. The sensor protein expressed in large scale was accumulated mainly in an insoluble fraction. The collected *E. coli* was disrupted by sonication and the insoluble fraction was collected by centrifugation. The insoluble fraction was dissolved with 8M urea, and the sensor protein having a histidine tag at its N-terminus was loaded on a Ni-NTA column, washed, and eluted by decreasing pH. Urea was removed from the fraction containing the protein of interest by dialysis to renature the sensor protein. On the other hand, BLIP gene was amplified by PCR using primers (Sequence Nos. 13 and 4) for adding 6 histidine residues to the N-terminus, digested with NdeI and SacI and inserted into the same site of the pEOR. *E. coli* JM109 having this plasmid was cultured in a 2xYT medium containing 100 μg/ml of carbenicillin, and BLIP was expressed in a large scale and purified.

Measurement of Fluorescence of Sensor Protein

Figure 4:
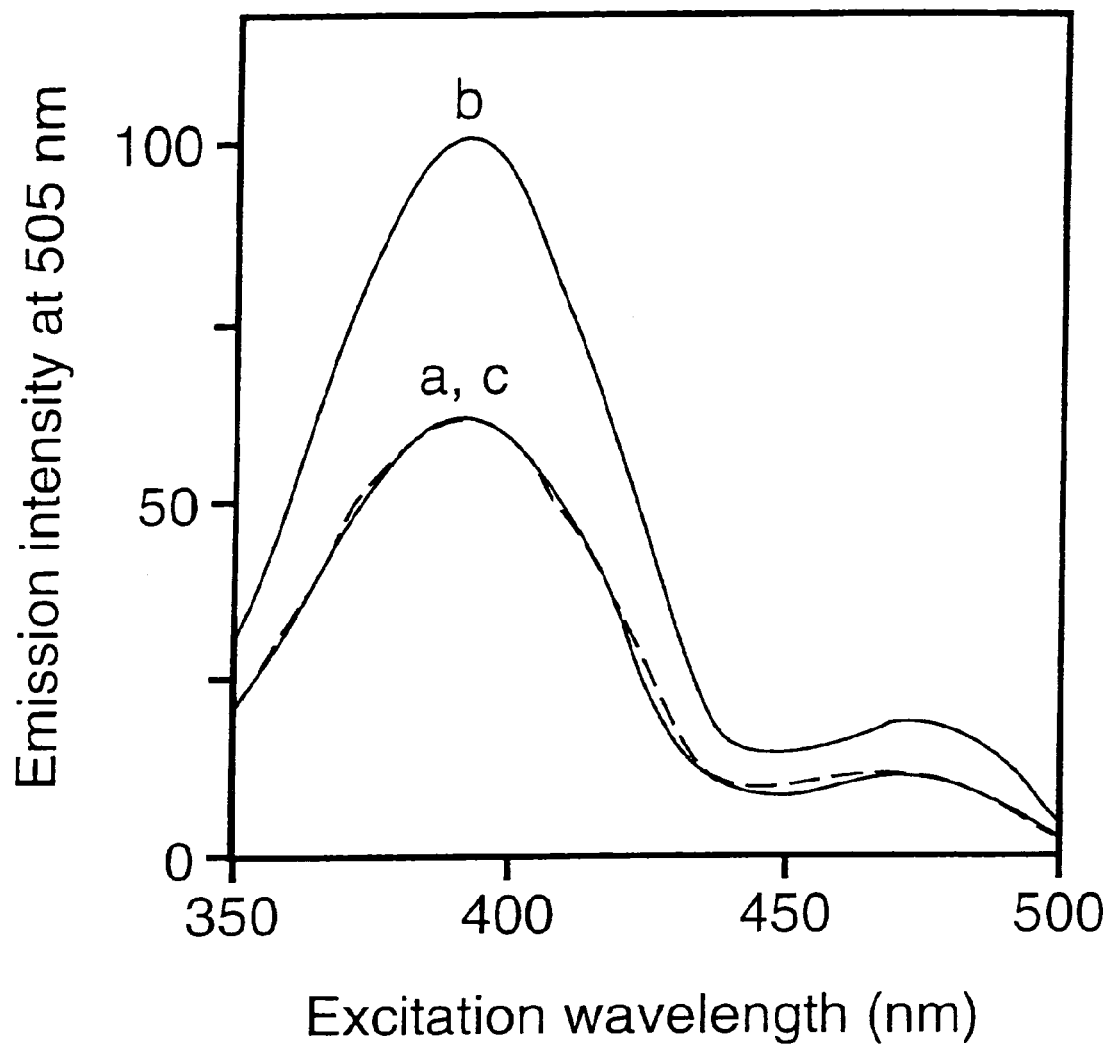
FIG. 4 is a graph showing fluorescent spectrum of a sensor protein. The horizontal axis in FIG. 4 represents an excitation wavelength and the vertical axis represents fluorescent intensity. In the figure, (a) represents the fluorescent spectrum for the sensor protein (a concentration of 0.3 $\mu$M), (b) represents the fluorescent spectrum when 7 $\mu$M of BLIP is added and (c) represents the fluorescent spectrum when 7 $\mu$M of bovine serum albumin (BSA) is added.

The fluorescence spectra of the sensor protein in the presence and absence of BLIP were respectively measured with Shimazu RF502 spectrofluorometer. The excitation spectrum at a radiation wave length of 505 nm of the sensor protein obtained by inserting β-lactamase into GFP indicated two absorption maxima around 395 nm and around 475 nm like wild type GFP (FIG. 4). When BLIP was added to this sensor protein, the intensity of fluorescence spectrum increased almost two times. However, when BSA was added as a control, no change of intensity was observed.

Titration Experiment of BLIP Concentration

Figure 5:
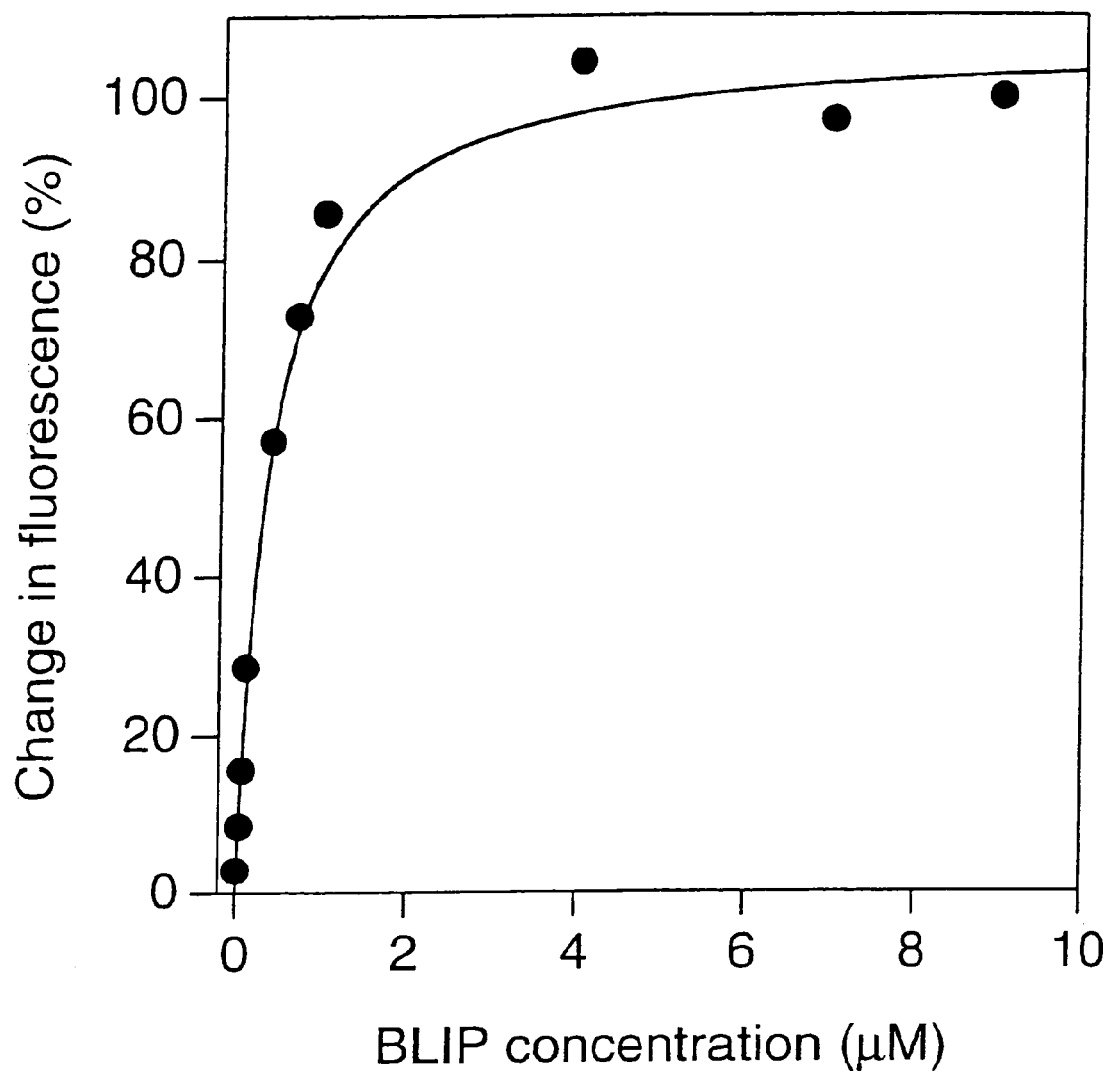
FIG. 5 is a graph showing dependency of fluorescent intensity of the sensor protein (GFP-β-lactamase insert-type fusion protein) of the present invention on the concentration of the target substance (BLIP). The horizontal axis in the figure represents the concentration of the target substance (BLIP) and the vertical axis represents change of the fluorescent intensity.

The dependency of fluorescence intensity of the sensor protein on BLIP concentration was examined. An amount of a change in fluorescence intensity at excitation wave length of 395 nm, ΔF, increased in a range of from 0.01 to 10 μM of BLIP concentration, [BLIP] (FIG. 5). The dissociation constant Kd was 0.35 μM, which was obtained by fitting the titration curve to a standard equation of:

$$\Delta F = \Delta F max/(1+Kd/[BLIP]),$$

and this value was well in agreement with the inhibition constant 0.2 μM of BLIP, which was obtained by the inhibition experiment of β-lactamase activity of the sensor protein. The above results demonstrate that the resultant insert-type fusion protein functioned as the sensor protein wherein the fluorescence intensity was changed by specific binding with BLIP.

Example 3

Preparation of Dioxin Sensor and Measurement of Dioxin Using the Same

Preparation of Dioxin Sensor

Figure 6:
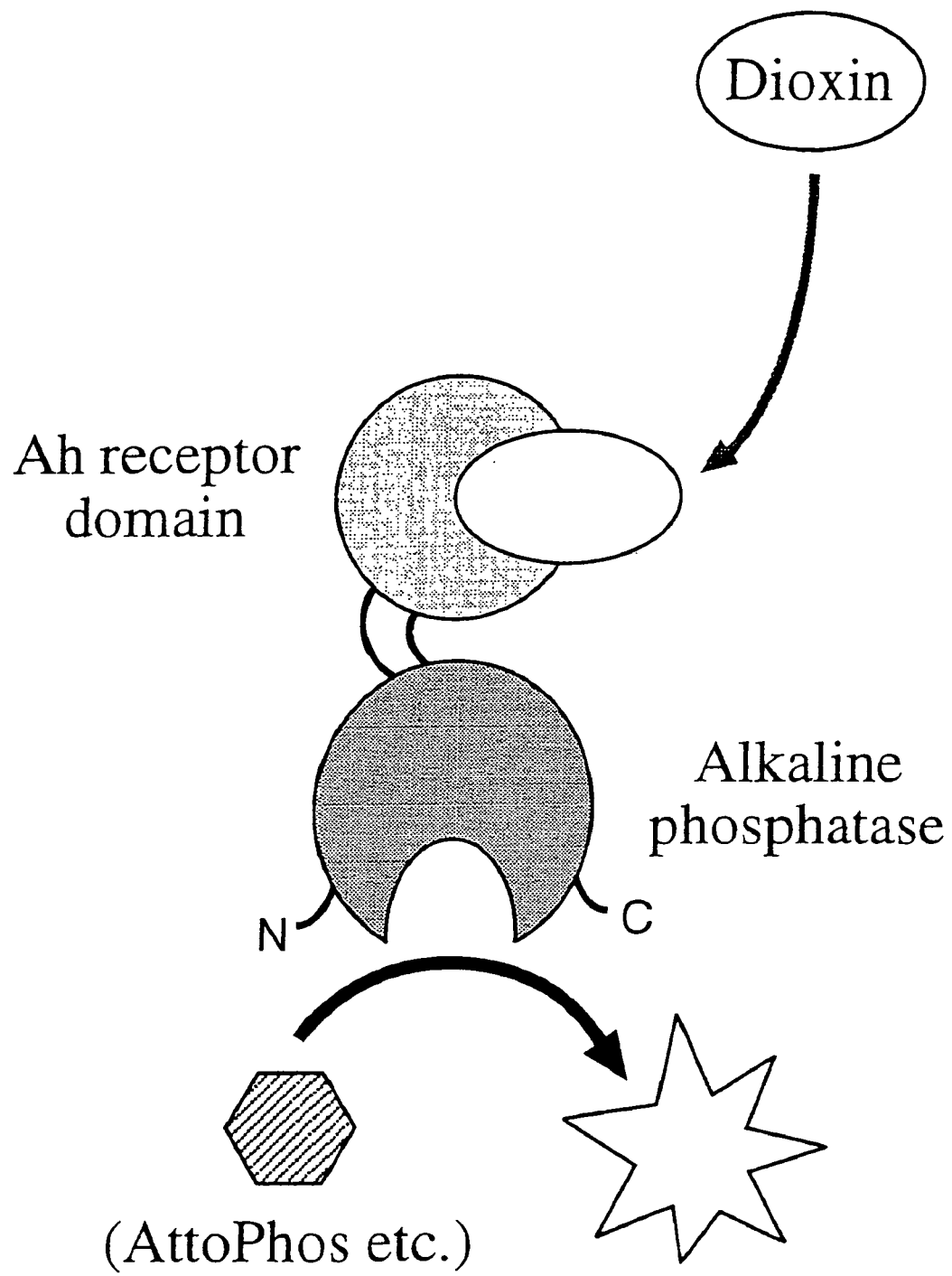
FIG. 6 is a schematic diagram showing measurement of dioxin by the use of a dioxin sensor of the present invention. When dioxin binds to the binding protein (Ah receptor domain), the structure of the protein is changed and the activity of the reporter protein (alkaline phosphatase) is correspondingly changed. The concentration of dioxin or the like can be determined by detecting such a change in the activity.

In accordance with the methods as described in Examples 1 and 2 above, sensor proteins against dioxins and PCB which are environmental pollutants, can be constructed. Specifically, the ligand-binding domain of an aryl hydrocarbon receptor (Ah receptor), which specifically binds with dioxins and PCB, is inserted into alkaline phosphatase which is an enzyme protein to construct an insert-type fusion protein (see FIG. 6). It is possible to detect or quantify dioxins by determining, as an indicator, a change in the alkaline phosphatase activity observed with binding of dioxins.

Construction of Plasmid

In order to introduce a restriction enzyme site for inserting an Ah receptor gene into an alkaline phosphatase gene (Chang et al. 1986. Gene 44, 121–125), DNA fragments of the N- and C-terminus of the alkaline phosphatase gene were amplified by PCR using the alkaline phosphatase gene as a template and appropriate two sets of primers, each of the DNA fragments was digested with appropriate two sets of restriction enzymes, and the DNA fragments thus digested were inserted at once into a plasmid containing an appropriate promoter. As the result, a restriction enzyme site can be introduced into a desired site in alkaline phosphatase.

Insertion of Ah Receptor and Screening

A DNA fragment containing the ligand-binding region of the Ah receptor (Kristine et al. 1993. Proc. Natl. Acad. Sci. USA 90, 8566–8570) is amplified by PCR using appropriate primers, digested with a restriction enzyme and inserted into the restriction enzyme site of the alkaline phosphatase gene on the plasmid. Further, a library formed by introducing a random mutation into the DNA encoding the insert-type fusion protein, is introduced into *E. coli* to allow the *E. coli* to form a colony on a LB plate. 96 colonies are cultured in a small amount of a liquid medium to induce expression of the mutant of the insert-type fusion protein in the *E. coli*. Respective mediums are dropped in a 96-well microtitre plate, and a cytolytic buffer containing lysozyme and EDTA is added to each well to disrupt *E. coli*. The fluorescent substrate for alkaline phosphatase is added thereto, and the enzyme activity is determined with a fluorescence plate reader. A mutant of the insert-type fusion protein wherein the enzyme activity undergoes a great change between the cases with and without addition of dioxins to the well is selected by screening.

Purification of Sensor Protein for Dioxin

The sensor protein which can be screened according to the above method and wherein the alkaline phosphatase activity undergoes a change by binding of dioxins, is expressed in a large scale and purified as follows. *E. coli* having a plasmid encoding the sensor protein is cultured in a suitable medium at an appropriate temperature until the absorbance at 600 nm reaches about 0.6 to 0.8, and then expression of the sensor protein is induced and cultivation is continued further for 3 to 5 hours. The collected *E. coli* is subjected to ultrasonic disruption, and the fraction containing the sensor protein collected by centrifugation is dissolved in an appropriate buffer. The fraction containing the sensor protein to which a histidine tags has been added at the N- or C-terminus is loaded on a Ni-NTA column, washed and then eluted from the column by decreasing pH or adding imidazole. The thus-purified sensor protein is stored at low temperature in a buffer containing an appropriate preservative such as glycerol.

Measurement of Dioxin Concentration by Sensor Protein

By using the sensor protein purified by the above method, the concentration of dioxins contained in a solution consisting of several components can be quantified. First, the sensor protein is added to a sample containing dioxins. The reaction mixture is left for an appropriate period of time to allow the Ah receptor domain of the sensor protein to bind to dioxins. In order to measure the change in the activity of alkaline phosphatase brought about as a result of binding, a fluorescent substrate for alkaline phosphatase (for example, AttoPhos) is added to the reaction solution and fluorescence generated by the hydrolyzed substrate is measured with a spectrofluorometer to estimate the amount of a change in the activity. On the basis of the table of data prepared by the titration experiment wherein amounts of a change in activity of dioxins having previously known concentrations are measured, the dioxin concentration in an unknown sample can be determined.

INDUSTRIAL APPLICABILITY

According to the present invention, there is provided a sensor protein wherein a binding protein is inserted into the amino acid sequence of a reporter protein, a method of constructing the same and a method of utilizing the same. According to the present invention, it becomes possible to provide sensor proteins that bind or interact with various kinds of target substances, and these sensor proteins can be utilized suitably, e.g., for detection or quantification of endocrine disrupting chemicals, for fluorescent molecule imaging in a living cell, and for a simple method of measuring an antigen-antibody reaction and the like.

What is claimed is:

1. A sensor protein comprising a fusion protein which comprises
a reporter protein which can generate a measurable signal selected from the group consisting of: Fluorescent Protein, alkaline phosphatase and kanamycin nucleotidyltransferase, or a fragment or mutant thereof, and
a binding protein which is 100 to 1000 amino acid residues in length, which specifically recognizes and binds a target substance, and which changes the structural stability of the fusion protein upon binding to the target substance, wherein the binding protein is inserted into the amino acid sequence of the reporter protein at an exposed site on the structural surface of the reporter protein, and wherein the insertion of the binding protein does not disrupt the ability of the reporter protein to generate the measurable signal.

2. The sensor protein according to claim 1 wherein the binding protein is selected from the group consisting of metal ion-binding proteins, DNA-binding proteins, cAMP-dependent protein kinase, cGMP-dependent protein kinase, hydrolase, ATP-binding proteins, GTP-binding proteins, nitric monoxide synthase, glucose-binding proteins, maltose-binding proteins, hormone receptors, single chain antibodies and chaperons; or a fragment thereof which changes the structural stability of the fusion protein upon binding to the target substance.

3. The sensor protein according to claim 1, wherein the fluorescent protein is Green Fluorescent Protein, Red Fluorescent Protein or a mutant thereof.

4. The sensor protein according to claim 1, wherein the reporter protein is the Green Fluorescent Protein and the binding protein is inserted between amino acid residues 128 Ile to 205 Ser of the Green Fluorescent Protein.

5. The sensor protein according to claim 1, which is comprised of a fusion protein, wherein the binding protein is an aryl hydrocarbon receptor and the reporter protein is alkaline phosphatase.

6. A method of preparing a sensor protein according to claim 1, comprising the steps of:
(a) inserting a DNA encoding a binding protein into a DNA sequence encoding a reporter protein which can generate a measurable signal,
wherein the binding protein is 100 to 1000 amino acid residues in length, and specifically recognizes and binds a target substance, and which changes the structural stability of the fusion protein upon binding to the target substance, wherein the binding protein is inserted into the amino acid sequence of the reporter protein at an exposed site on the structural surface of the reporter protein, and wherein the insertion of the binding protein does not disrupt the ability of the reporter protein to generate the measurable signal, and wherein the reporter protein is selected from the group consisting of: Fluorescent Protein, alkaline phosphatase and kanamycin nucleotidyltransferase, or a fragment or mutant thereof; and (b) expressing the resultant DNA encoding the fusion protein.

7. A method of preparing a sensor protein according to claim 1, comprising the steps of:

(a) inserting a DNA encoding a binding protein into a DNA sequence encoding a reporter protein which can generate a measurable signal, wherein the binding protein is 100 to 1000 amino acid residues in length, and specifically recognizes and binds a target substance, and which changes the structural stability of the fusion protein upon binding to the target substance, wherein the binding protein is inserted into the amino acid sequence of the reporter protein at an exposed site on the structural surface of the reporter protein, and wherein the insertion of the binding protein does not disrupt the ability of the reporter protein to generate the measurable signal, and wherein the reporter protein is selected from the group consisting of: Fluorescent Protein, alkaline phosphatase and kanamycin nucleotidyltransferase, or a fragment or mutant thereof; and (b) introducing a mutation into the resultant DNA sequence encoding the fusion protein to obtain a population of mutants of the DNA sequence encoding the fusion protein;

(c) expressing the population of mutants of the DNA sequence encoding the fusion protein to obtain a population of mutants of the fusion protein; and (d) selecting the fusion protein having the desired function from the population of mutants of the fusion protein by detecting a change in the detection signal generated from the reporter protein by the action of a target substance to the binding protein.

8. A sensor protein according to claim 1 prepared by the method according to any one of claims 6 to 7.

9. The sensor protein according to claim 1, wherein the reporter protein is the Green Fluorescent Protein and the binding protein is a hormone receptor.

10. The sensor protein according to claim 9, wherein the hormone receptor is an aryl hydrocarbon receptor.

* * * * *